United States Patent [19]

Worthington et al.

[11] Patent Number: 4,690,941

[45] Date of Patent: * Sep. 1, 1987

[54] CERTAIN TRIAZOLE COMPOUNDS AND THEIR USE AS FUNGICIDES

[75] Inventors: Paul A. Worthington; Margaret C. Shephard, both of Maidenhead, England

[73] Assignee: Imperial Chemical Industries PLC, London, England

[*] Notice: The portion of the term of this patent subsequent to Sep. 18, 2001 has been disclaimed.

[21] Appl. No.: 745,780

[22] Filed: Nov. 29, 1976

[30] Foreign Application Priority Data

Dec. 3, 1975 [GB] United Kingdom ............... 49656/75
Nov. 16, 1976 [GB] United Kingdom ............... 47666/76

[51] Int. Cl.⁴ ................... C07D 249/08; A01N 43/64
[52] U.S. Cl. ................... 514/383; 548/262; 548/101; 71/76; 71/92
[58] Field of Search ................... 260/308 R; 424/269; 548/262

[56] References Cited

U.S. PATENT DOCUMENTS

| | | | |
|---|---|---|---|
| 3,394,143 | 7/1968 | Wolf | 260/308 |
| 3,701,784 | 10/1972 | Seidel et al. | 424/269 |
| 3,952,002 | 4/1976 | Kramer et al. | 424/269 |
| 4,315,016 | 2/1982 | Balasubramanyan et al. | 548/262 |
| 4,394,380 | 7/1983 | Balasubramanyan et al. | 548/262 |
| 4,598,085 | 7/1986 | Heeres et al. | 548/262 |

FOREIGN PATENT DOCUMENTS 2431407 12/1975 Fed. Rep. of Germany ...... 548/262

*Primary Examiner*—Glennon H. Hollrah
*Assistant Examiner*—D. L. Dinner
*Attorney, Agent, or Firm*—Cushman, Darby & Cushman

[57] ABSTRACT

A compound of the formula:

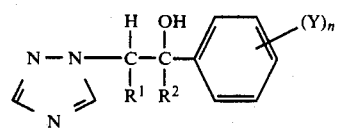

wherein $R^1$ is hydrogen, $C_1$–$C_8$ alkyl, unsubstituted benzyl or benzyl substituted with halogen methyl, ethyl, propyl, butyl, nitro, trifluoromethyl, cyano, methoxy, ethoxy, phenyl or methylenedioxy; $R^2$ is hydrogen or $C_1$–$C_8$ alkyl; Y is hydrogen, halogen, nitro, $C_{1-4}$ alkyl, $C_{1-4}$ alkoxy unsubstituted amino or methyl- or ethyl-substituted amino, and n is 1 or 2; each of the groups Y being the same or different when n is 2 and Y being other than hydrogen or halogen when $R^1$ and $R^2$ are both hydrogen; or a fungicidal acid salt or metal complex of said compound. Fungicidal compositions containing these compounds and methods of using the same to combat plant fungal diseases are also disclosed.

5 Claims, No Drawings

CERTAIN TRIAZOLE COMPOUNDS AND THEIR USE AS FUNGICIDES

This invention relates to certain heterocyclic compounds which are 1,2,4-triazole compounds, to a process for preparing them, to plant anti-fungal compositions containing them and to a method of combating fungal diseases in the plants using The 1,2,4-triazole compounds have the general formula:

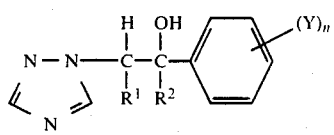

wherein each of $R^1$ and $R^2$, which may be the same or different, is hydrogen or optionally-substituted hydrocarbyl; Y is hydrogen, halogen (e.g. fluorine, chlorine, bromine or iodine), nitro, lower alkyl (e.g. methyl or ethyl), lower alkoxy (e.g. methoxy or ethoxy) or optionally substituted amino, and n is an integer of 1 to 5; each of the groups Y being the same or different when n is greater than 1 and Y being other than hydrogen or halogen when $R^1$ and $R^2$ are both hydrogen; and salts and metal complexes thereof.

The compounds of the invention contain chiral centres. The compounds are generally obtained in the form of racemic mixtures. However these and other mixtures can be separated into the individual isomers by methods known in the art.

The hydrocarbyl may be saturated or unsaturated, straight or branched chain or single ring or multi-ring; examples are alkyl, alkenyl, alkynyl, cycloalkyl, aryl, aralkyl or alkaryl.

When a hydrocarbyl group is, or contains, an aryl group (e.g. it is benzyl or phenyl), the latter can be ring-substituted by halogen, alkyl [e.g. methyl, ethyl, propyl (n- or i-propyl) and butyl (e.g. n-, i- or t-butyl) ], nitro, trifluoromethyl, cyano, alkoxy (e.g. methoxy or ethoxy), phenyl or alkylenedioxy (e.g. methylenedioxy). The benzyl (and other aralkyl groups) can also be substituted on their alkyl moieties; examples of suitable substituents are alkyl and phenyl.

The hydrocarbyl is suitably $C_{1-8}$, e.g. $C_{1-7}$, hydrocarbyl; examples are methyl, ethyl, propyl (n- or i-propyl), butyl (n-, i- or t-butyl), amyl (e.g. isopentyl), hexyl (e.g. 3,3-dimethylbutyl), heptyl, allyl, propynyl (e.g. propargyl), phenyl, tolyl, nitrophenyl, chlorophenyl, benzyl itself, α-(methyl or phenyl)-benzyl, α-methyl-4-chlorobenzyl, chlorobenzyl (e.g. 2- or 4-chlorobenzyl or 3,4- or 2,4-dichlorobenzyl), fluorobenzyl (e.g. 2-, 3- or 4-fluorobenzyl) or nitrobenzyl (e.g. 4-nitrobenzyl), (trifluoromethyl)benzyl, chloronitrobenzyl or p-phenylbenzyl.

Y is preferably fluorine or chlorine, and n is 1 or 2. When n is 1, Y is preferably in the 4-position. When Y is substituted amino, it can be mono- or di-substituted with, for example, alkyl (e.g. methyl or ethyl).

Suitable salts are those with organic or inorganic acids, e.g. hydrochloric, sulphuric, nitric, acetic or oxalic acid. Suitable metal complexes are those with copper, zinc, manganese and iron.

Specific examples of the compounds of general formula (I) are shown in Table I, wherein n is 1.

TABLE I

| COMPOUND NO | $R^1$ | $R^2$ | Y | M.P. (°C.) | STEROCHEMISTRY |
| --- | --- | --- | --- | --- | --- |
| 1 | n-Bu | H | 4-Cl | 93–94° | One isomer |
| 2 | n-Bu | H | 4-Cl | white oil | Mixture* |
| 3 | 2,4-di-Cl-benzyl | H | H | 115–119° | Mixture* |
| 4 | benzyl | H | H | 103–106° | Mixture* |
| 5 | 2,4-di-Cl-benzyl | H | 4-Cl | 112–115° | One isomer |
| 6 | 2-F-benzyl | H | 4-Cl | 129–132° | One isomer |
| 7 | benzyl | H | 4-Cl | 176–177° | One isomer |
| 8 | 2,4-di-Cl-benzyl | H | 4-F | 142–145° | One isomer |
| 9 | α-Ph-benzyl | H | 4-Cl | 157–159° | One isomer |
| 10 | α-Me-benzyl | H | 4-Cl | 75–82° | + |
| 11 | 4-F-benzyl | H | 4-Cl | 123–127° | One isomer |
| 12 | n-Bu | H | H | 68–70° | One isomer |
| 13 | 4-F-benzyl | Me | 4-Cl | 145° | One isomer |
| 14 | α-Me-benzyl | H | H | | |
| 15 | 3-F-benzyl | H | 4-Cl | | |

*A mixture (3:2) of the two diastereoisomers
+A mixture of a number of isomers

The compounds of the invention wherein $R^2$ is hydrogen may be made by reducing a ketone of general formula (II):

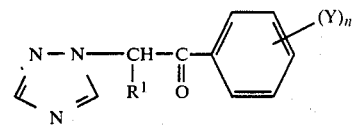

wherein $R^1$, Y and n are as defined above, or a salt thereof, with a metal hydride reducing agent (e.g. lithium aluminium hydride or sodium borohydride in an inert solvent. If desired, catalytic hydrogenation using a suitable metal catalyst can be used.

As implied in Table I above, the compounds of the invention are obtained sometimes in the form of a single diastereoisomer and sometimes in the form of an isomeric mixture (e.g. a mixture of two diasteroeoisomers). Whether there is formed a single isomer or a mixture of isomers appears to depend on the nature of the reducing agent used. When $R^1$ is alkyl, lithium aluminium hydride gives a single isomer while sodium borohydride gives the mixture.

The reduction can be performed by dissolving the reactants in a solvent such as diethyl ether or tetrahydrofuran (for lithium aluminium hydride reduction) or water (for sodium borohydride reduction). The reaction temperature will depend on the reactants and solvent; but generally the reaction mixture is heated under reflux. After the reaction, the product can be isolated by extraction into a convenient solvent after acidification with dilute mineral acid. On removal of the solvent in vacuo, the product may be crystallised from a convenient solvent.

The compounds of general formula (I) wherein $R^2$ is hydrocarbyl, or a salt thereof, can be prepared by reacting a compound of general formula (II) or a salt thereof with the appropriate Grignard reagent e.g. an alkyl magnesium halide such as methyl magnesium bromide or iodide. This reaction can be performed by methods known in the art.

The starting compound of general formula (II) may be made by reacting 1,2,4-triazole or a salt thereof with a α-haloketone of general formula (III)

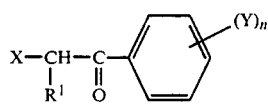

wherein X is halogen, preferably bromine or chlorine, and $R^1$, Y and n are as defined above. This process may be carried out by heating the reactants together in the absence of a solvent or diluent, but preferably a solvent is present.

Suitable solvents are non-hydroxylic solvents such as acetonitrile, dimethylformamide, dimethyl sulfoxide, sulpholane and tetrahydrofuran. Hydroxylated solvents, for example, methanol and ethanol, may be used in certain circumstances when the presence of the hydroxyl group does not interfere with the reaction. The process can be carried out in the presence of a base such as sodium hydride, sodium ethoxide, excess triazole, or an alkali metal carbonate (e.g. potassium carbonate). The reaction temperature will depend upon the choice of reactants, solvents and base, but generally the reaction mixture is heated under reflux. The process generally consists of dissolving the reactants in a solvent and then isolating the product by removal of the reactant solvent in vacuo. Unreacted triazole can be removed by extraction of the product with a suitable solvent which is then washed with water. A crystallisation or other purification procedure may then be carried out if desired.

The α-halo ketones may be made by any of the methods set out in literature.

The compounds are active fungicides, particularly against the diseases:

*Piricularia oryzae* on rice

*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants

*Erysiphe graminis* (powdery mildew) on barley and wheat and other powdery mildews on various hosts such as *Sphaerotheca fuliginea* on cucurbits (e.g. cucumber), *Podophaera leucotricha* on apples and *Uncinula necator* on vines

*Venturia inaequalis* (scab) on apples

*Botrytis cinerea* (grey mould) on tomatoes, strawberries, vines and other hosts Some of the compounds have also shown a broad range of activities against fungi in vitro. Further some of the compounds are active as seed dressings against: Fusarium spp., Septoria spp., Tilletia spp., Ustilago spp., and Pyrenophora spp. on cereals.

The compounds also have certain plant growth regulating activities (particularly a stunting effect on the vegetative growth of mono- and di-cotyledonous plants), and anti-bacterial and anti-viral activities as well as herbicidal activity.

The compounds may be used as such for fungicidal purposes but are more conveniently formulated into compositions for such usage. The invention thus provides also a fungicidal composition comprising a compound of general formula (I) or a salt or complex thereof and a carrier or diluent.

The invention also provides a method of combating fungal diseases in a plant, which method comprises applying to the plant, to seed of the plant or to the locus of the plant or seed a compound or salt or complex thereof as hereinbefore defined.

The compounds can be used to combat plant fungi and treat plants or seeds in a number of ways, for example they can be applied, formulated or unformulated, directly to the foliage of a plant which is infected or likely to become infected, or they can be applied also to bushes and trees, to seeds or to other medium in which plants, bushes or trees are growing or are to be planted, or they can be sprayed on, dusted on or applied as a cream or paste formulation. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersions or emulsions may be prepared by dissolving the active ingredient(s) in a organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes and trichloroethylene.

The compositions to be used as sprays may also be in the form of aerosols wherein the formulation is held in a container under pressure in the presence of a propellant, e.g. fluorotrichloromethane or dichlorodifluoromethane.

By including suitable additives, for example additives for improving the distribution, adhesive power and resistance to rain on treated surfaces, the different compositions can be better adapted for various utilities.

The compounds can be used as mixtures with fertilisers (e.g. nitrogen - or phosphorus - containing fertilisers). Compositions comprising only granules of fertiliser incorporating, for example coated with, the compound, are preferred. The invention therefore also provides a fertiliser composition comprising the compound of general formula (I) or a salt or complex thereof.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or nonanionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain 10–85%, generally 25–60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity (e.g. growth stimulating substances such as the gibberellins and other compounds having complementary fungicidal or insecticidal activity), as well as stabilising agent(s), for example epoxides (e.g. epichlorhydrin).

The following Examples illustrate the invention; the temperatures are given in degrees Centigrade (°C).

EXAMPLE 1

2-(1,2,4-Triazol-1-yl)-1-(4'-chlorophenyl)hexan-1-ol (Compound 1)

Stage 1: Bromine (0.02 mol) was added dropwise to a stirred solution of 4'-chlorohexanophenone (0.02 mol) in dry diethyl ether (20 ml) at 10°–20° over one hour. The ether was then removed in vacuo from the reaction mixture to leave a pale-yellow liquid which on distillation gave 2-bromo-4'-chlorohexanophenone, b.p. 124°–126°/0.04 mm Hg.

Stage 2: 2-Bromo-4'-chlorohexanophenone (0.02 mol), 1,2,4-triazole (0.10 mol) and acetonitrile (50 ml) were refluxed for 48 hours. The acetonitrile was removed in vacuo and the residue extracted with chloroform (150 ml), washed with water (5×100 ml) and dried over anhydrous sodium sulphate. The solvent was removed in vacuo to leave an oil which crystallised on trituration with petroleum ether (5×50 ml). Recrystallisation from petroleum ether gave 2-(1,2,4-triazol-1-yl)-2-n-butyl-4'-chloroacetophenone, m.p. 81°–83°.

Analysis: $C_{14}H_{16}ON_3Cl$ Requires: C, 60.4%; H, 5.8%; N, 15.1%; Found: C, 59.6%; H, 5.6%; N, 15.5%.

Stage 3: The product (0.01 mol) of Stage 2 was added portionwise to a suspension of lithium aluminium hydride (0.005 mol) in diethyl ether (10 ml; dried over sodium) to maintain refluxing. The ethereal solution was refluxed for a further four hours; the excess lithium aluminium hydride was quenched with water (20.0 ml) and the mixture acidified with concentrated sulphuric acid. The ethereal layer was washed with water (4×25 ml) and dried over anhydrous sodium sulphate. Removal of the ether gave an oil which solidified on standing. Recrystallisation from methylene chloride/petroleum ether gave the title compound as a white solid, m.p. 93°–94°.

Analysis: $C_{14}H_{18}ON_3Cl$ Requires : C, 60.1%; H, 65%; N, 15.0%; Found : C, 59.4%; H, 6.3%; N, 14.7%.

EXAMPLE 2

1-(4'-chlorophenyl)-2-(1,2,4-triazol-1-yl)-3-(2',4'-dichlorophenyl)-propan-1-ol (Compound 5 )

Sodium borohydride (0.42 g) was added in small portions to 2-(1,2,4-triazol-1-yl)-2-(2',4'-dichlorobenzyl)-4'chloroacetophenone (4.2 g) in methanol (40 ml). When the effervescence ceased, the mixture was refluxed for 1 hour, cooled to room temperature and the methanol removed at the water pump. The residue was acidified with 1N-hydrochloric acid to give a solid which was filtered and washed. Recrystallisation from ethanol/water gave white crystals of the title compound (yield 80%).

Analysis: $C_{17}H_{14}ON_3Cl_3$ Requires : C, 53.3%; H, 3.7%; N, 11.0%; Found: C, 53.6%; H, 3.7%, N, 11.1%.

EXAMPLE 3

The compounds were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots.

The test compounds were formulated either by bead-milling with aqueous Dispersol T or as a solution in acetone/ethanol which was diluted to the required concentration immediately before use. For the foliage diseases, 100 p.p.m. a.i. suspensions were sprayed on to the foliage and applied to the roots of the same plant via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil (roots) and/or to the foliage (by spraying) one or two days before the plant was inoculated with the diseases. An exception was the test on *Erysiphe graminis*, in which the plants were inoculated 24 hours before treatment. After inoculation, the plants were put into an appropriate environment to allow infection to take place and then incubated until the disease was ready for assessment. The period between inoculation and assessment varied from 4 to 14 days according to the disease and environment.

The disease control was recorded by the following grading:
4=No disease
3=0-5%
2=6-25%
1=26-60%
0=>60%

The results are shown in Table II.

TABLE II

| | DISEASE CONTROL | | | | | |
|---|---|---|---|---|---|---|
| COMPOUND NO | Puccinia recondita in wheat | Phytophthora infestans in tomato | Plasmopara viticola in vines | Piricularia oryzae in rice | Botrytis cinerea in tomatoes | Erysiphe graminis in barley |
| 1 | 3 | 0 | 0 | 0 | 0-2 | 4 |
| 2 | 3 | 0 | 0 | 0 | 0-2 | 4 |
| 3 | 0 | 0 | 0 | 0 | 0-3 | 4 |
| 4 | 4 | 0 | 0 | 1-2 | 0 | 4 |
| 5 | 3 | 0 | 0 | 0 | 2-3 | 3 |
| 6 | 4 | 0 | 0 | 0 | 1 | 4 |
| 7 | 4 | 0 | 0 | 0 | 2-3 | 4 |
| 8 | 3 | 0 | 1-2 | 0 | 0 | 4 |
| 9 | 3-4 | 0 | 0 | 1-2 | 0 | 4 |
| 10 | 4 | 1 | 0 | 0 | 0 | 4 |

We claim:

1. A compound of the formula

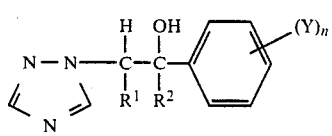

wherein $R^1$ is butyl or benzyl; $R^2$ is hydrogen; Y is hydrogen, halogen, nitro, $C_{1-4}$ alkyl, $C_{1-4}$ alkoxy or unsubstituted amino, and n is 0, 1 or 2; or a fungicidal acid salt of said compound.

2. A compound as claimed in claim 1 wherein Y is hydrogen or n is 1 and Y is halogen in the 4-position.

3. A compound as claimed in claim 2 wherein $R^1$ is n-butyl and Y is chlorine in the 4-position.

4. A fungicidal composition consisting essentially of, as active ingredient, a fungicidally effective amount of a compound, salt or complex as claimed in claim 1, and a inert carrier for the active ingredient.

5. A method of combating fungal diseases in a plant, the method consisting essentially of the step of applying to the plant, to seed of the plant or to the locus of the plant or seed, a fungicidally effective amount of a compound of the formula:

ps wherein $R^1$ is butyl or benzyl; $R^2$ is hydrogen; Y is hydrogen, halogen, nitro, $C_{1-4}$ alkyl, $C_{1-4}$ alkoxy or unsubstituted amino, and n is 0, 1 or 2; or a fungicidal acid salt of said compound.

* * * * *